(12) United States Patent
O'Brien et al.

(10) Patent No.: US 10,034,688 B2
(45) Date of Patent: Jul. 31, 2018

(54) CERVICAL CERCLAGE ASSISTANCE DEVICE

(71) Applicant: Cook Medical Technologies LLC, Bloomington, IN (US)

(72) Inventors: John M. O'Brien, Lexington, KY (US); Jorge Jimenez-Rios, Bloomington, IN (US); Lyle Hundley, Bloomington, IN (US); Kate Duncan, Mooresville, IN (US); Melissa Dale, Linton, IN (US); Matthew J. Terwiske, Bloomington, IN (US)

(73) Assignee: Cook Medical Technologies LLC, Bloomington, IN (US)

( * ) Notice: Subject to any disclaimer, the term of this patent is extended or adjusted under 35 U.S.C. 154(b) by 208 days.

(21) Appl. No.: 14/879,568

(22) Filed: Oct. 9, 2015

(65) Prior Publication Data

US 2016/0106467 A1 Apr. 21, 2016

Related U.S. Application Data

(60) Provisional application No. 62/065,996, filed on Oct. 20, 2014.

(51) Int. Cl.
*A61B 17/44* (2006.01)
*A61B 17/08* (2006.01)
(Continued)

(52) U.S. Cl.
CPC ............ *A61B 17/442* (2013.01); *A61B 17/42* (2013.01); *A61B 17/12* (2013.01);
(Continued)

(58) Field of Classification Search
CPC ....... A61B 17/442; A61B 17/42; A61B 17/12; A61B 2017/4216; A61B 2017/4225; A61F 6/204; A61F 6/202
(Continued)

(56) References Cited

U.S. PATENT DOCUMENTS

| 4,128,100 A | 12/1978 | Wendorff |
| 4,592,339 A * | 6/1986 | Kuzmak ................. A61B 17/12 128/899 |

(Continued)

FOREIGN PATENT DOCUMENTS

| CA | 2 866 316 | 9/2013 |
| CN | 201806769 U | 4/2011 |

(Continued)

OTHER PUBLICATIONS

International Search Report for PCT/US2013/030320, dated Dec. 7, 2013, 11 pp.
(Continued)

*Primary Examiner* — Julian W Woo
(74) *Attorney, Agent, or Firm* — Brinks Gilson & Lione

(57) ABSTRACT

A medical device for interacting with a patient's cervix is provided. The device includes a grasper configured to allow gripping and compression of a patient's cervix when disposed proximate a patient's cervix and an elongate catheter comprising a distal portion that is selectively releasably connectable to the grasper. The grasper is adapted to interact with at least a portion of a patient's cervix when deployed, and a flexible member that extends from a first end portion of the grasper, with a proximal end portion retained by the grasper and an opposite distal end portion extending away from the grasper to a distal tip.

20 Claims, 16 Drawing Sheets

(51) Int. Cl.
*A61B 17/42* (2006.01)
*A61F 6/20* (2006.01)
*A61B 17/12* (2006.01)

(52) U.S. Cl.
CPC ............ *A61B 2017/4216* (2013.01); *A61B 2017/4225* (2013.01); *A61F 6/202* (2013.01); *A61F 6/204* (2013.01)

(58) Field of Classification Search
USPC .................................................... 606/74, 151
See application file for complete search history.

(56) References Cited

U.S. PATENT DOCUMENTS

| | | | |
|---|---|---|---|
| 5,160,338 A * | 11/1992 | Vincent | A61B 17/12 600/3 |
| 5,304,188 A | 4/1994 | Marogil | |
| 5,591,203 A | 1/1997 | Fahy | |
| 5,925,059 A | 7/1999 | Palermo et al. | |
| 6,063,100 A | 5/2000 | Diaz et al. | |
| 6,511,490 B2 * | 1/2003 | Robert | A61B 17/135 606/151 |
| 6,676,674 B1 * | 1/2004 | Dudai | A61B 17/12 606/151 |
| 7,105,007 B2 | 9/2006 | Hibler | |
| 8,523,886 B2 * | 9/2013 | Grigoryants | A61B 17/0469 606/139 |
| 2003/0236536 A1 | 12/2003 | Grigoryants et al. | |
| 2004/0092847 A1 | 5/2004 | Welch | |
| 2004/0127931 A1 | 7/2004 | Kincaid et al. | |
| 2005/0125006 A1 | 6/2005 | Nady | |
| 2005/0277948 A1 | 12/2005 | Cedars et al. | |
| 2007/0142844 A1 | 6/2007 | Kotmel et al. | |
| 2008/0188863 A1 | 8/2008 | Chu | |
| 2009/0306588 A1 | 12/2009 | Nguyen et al. | |
| 2011/0079226 A1 | 4/2011 | Sakhel | |
| 2013/0103044 A1 | 4/2013 | Brown | |
| 2013/0239974 A1 | 9/2013 | O'Brien et al. | |

FOREIGN PATENT DOCUMENTS

| | | |
|---|---|---|
| CN | 202 920 311 U | 6/2013 |
| DE | 43 02 895 A1 | 8/1994 |
| WO | WO 2013/138263 A1 | 9/1913 |
| WO | WO 2006/117612 A1 | 11/2006 |
| WO | WO 2010/114577 A1 | 10/2010 |

OTHER PUBLICATIONS

International Preliminary Report on Patentability and Written Opinion for PCT/US2013/030320, dated Sep. 16, 2014, 7 pp.
Patent Examination Report, IP Australia, for AU 2013232405, dated Jan. 13, 2015, 3 pp.
European Search Report for EP 15 19 0350, dated Feb. 18, 2016, 7 pp.
IP Australia Examination Report No. 1 for Application No. 2015243112, dated Feb. 16, 2017, 5 pp.
IP Australia Communication Pursuant to Article 94(3) EPC for Application No. 15 190 350.7, dated Mar. 20, 2018, 5 pp.

* cited by examiner

CERVICAL CERCLAGE ASSISTANCE DEVICE

CROSS-REFERENCE TO RELATED APPLICATIONS

This application claims priority from U.S. Provisional Application No. 62/065,996, filed on Oct. 20, 2014, the entirety of which is hereby fully incorporated by reference herein.

TECHNICAL FIELD

The cervical cerclage procedure is often indicated for expecting female patients that have an incompetent cervix, or a cervix that is incapable of remaining closed during pregnancy, prior to the onset of labor. The cerclage procedure most often involves the physician vaginally suturing the patient's cervical tissue closed, or to the neighboring portions of the cervical tissue to prevent fluid or other communication through the cervix and into or out of the uterus prior to the onset of labor. There are several common types of vaginal cerclage stitches, such as the McDonald stitch and the Shirdokar stitch. While these types of cerclage stitches are well known in the art, they are often difficult to perform due to the number of instruments needed to both prepare and compress the cervical tissue to close the cervix prior to the cervical stitching, as well the needles needed to perform the cerclage stitch itself. The patient's vagina includes a relatively small space for all of these tools and therefore the cerclage procedure is overly complicated and time consuming.

BRIEF SUMMARY

A first representative embodiment of the disclosure is provided. The embodiment includes a medical device. The medical device includes a grasper configured to allow gripping and compression of a patient's cervix when disposed proximate a patient's cervix and an elongate catheter comprising a distal portion that is selectively releasably connectable to the grasper, the grasper includes at least one leg and is adapted to interact with at least a portion of a patient's cervix when deployed, and a flexible member that extends from a first end portion of the grasper with a proximal end portion retained by the grasper and an opposite distal end portion extending away from the grasper to a distal tip.

A second representative embodiment of the disclosure is provided. The second embodiment includes a medical device. The medical device includes a grasper configured to allow gripping and compression of a patient's cervix when disposed proximate a patient's cervix. An elongate catheter is provided and includes a distal portion that is selectively releasably connectable to the grasper, the grasper is adapted to interact with at least a portion of a patient's cervix when deployed. A flexible member extends from a first end portion of the grasper, with a proximal end portion retained by the grasper and an opposite distal end portion extending away from the grasper to a distal tip. The flexible member comprises a plurality of retention features that are spacingly disposed along a length of the flexible member between the distal tip and the proximal end portion and the arcuate member further comprises a second end portion, the second end portion includes a receiving structure that is arranged to interact and retain a portion of the flexible member. A distal tip of the catheter includes a hollow portion, and wherein when the catheter is connected to the grasper, a proximal portion of the grasper is disposed within the hollow portion.

Advantages of the present disclosure will become more apparent to those skilled in the art from the following description of the preferred embodiments of the disclosure that have been shown and described by way of illustration. As will be realized, the disclosed subject matter is capable of other and different embodiments, and its details are capable of modification in various respects. Accordingly, the drawings and description are to be regarded as illustrative in nature and not as restrictive.

BRIEF DESCRIPTION OF THE DRAWINGS

FIG. 3b is a view of detail D of FIG. 3a.

DETAILED DESCRIPTION OF THE DRAWINGS AND THE PRESENTLY PREFERRED EMBODIMENTS

Figure 1:
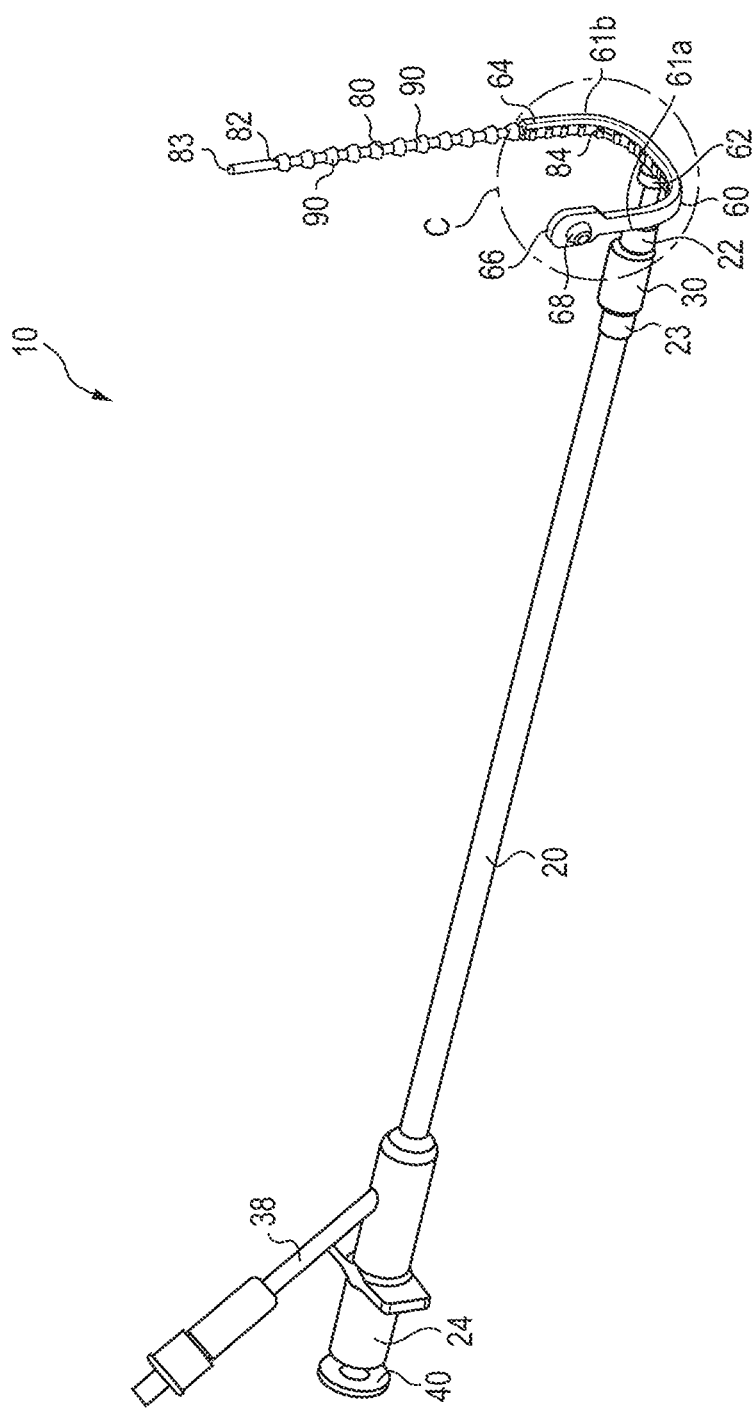
FIG. 1 is a perspective view of a cervical cerclage assistance device, showing a balloon disposed upon a catheter in a deflated configuration.
Figure 2:
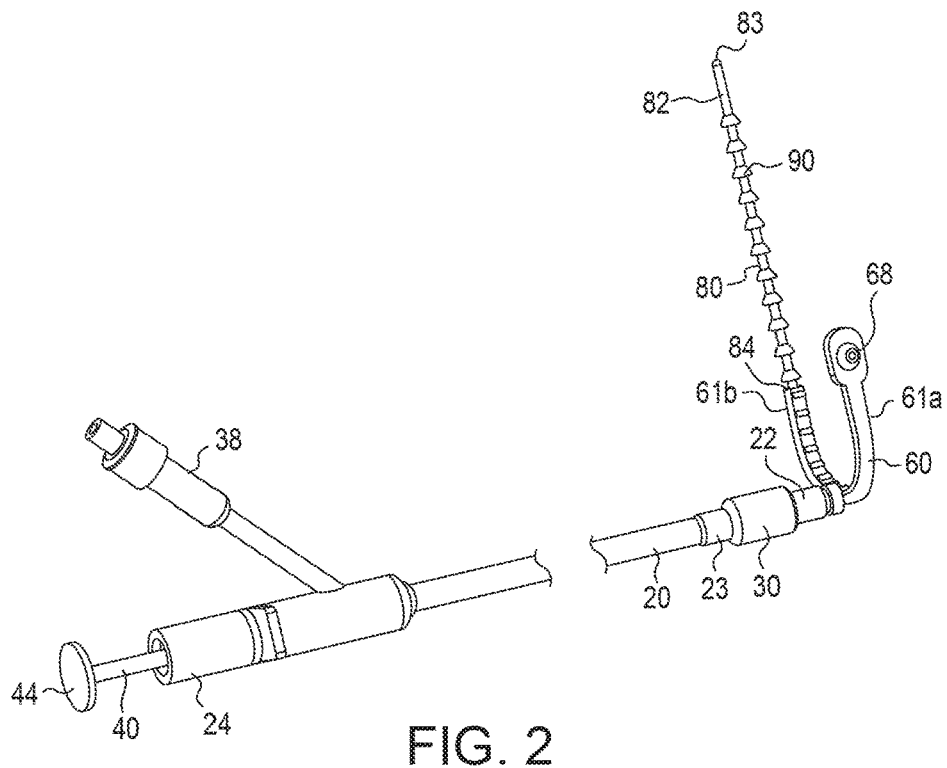
FIG. 2 is another perspective of the device of FIG. 1.

Turning now to FIGS. 1-17, a cerclage assistance device 10 is provided. The device 10 includes a catheter 20 that extends from a proximal end portion 24 to a distal end portion 22. An inflatable balloon 30, similar to a Foley balloon, is provided at the distal end portion 22. A first lumen 27 is disposed along the length of the catheter 20 to allow for selective inflation of the balloon 30 from the proximal end portion 24 of the catheter 20. The proximal end portion 24 of the catheter may receive a syringe through a luer lock fitting 38 or similar structure that is disposed in fluid communication with the first lumen 27 to allow for selective inflation and deflation of the balloon 30. The catheter 20 may additionally include a second lumen 21 along its length between the proximal and distal end portions 24, 22 to allow a stylet 40 to slidingly pass therethrough. The distal end portion 22 of the catheter 20 includes a hollow portion 21a that communicates with the second lumen 21.

The catheter 20 is releasably engaged with a grasper 60 at the distal end portion 22 of the catheter 20. The grasper 60 may include a proximal portion 62 from which a finger 63 extends. The finger 63 selectively mates with a corresponding finger 43 of the stylet 40, discussed in detail below, to connect the grasper 60 to the stylet 40 and ultimately to the catheter 20.

The grasper 60 may include an arcuate member 61 that is fixed to the proximal member 62, and the arcuate member 61 may include first and second legs (or arms) 61a, 61b that extend from the proximal portion 62 to establish a generally U shaped profile, while in other embodiments, the legs may extend to establish a V shaped profile, or in still other embodiments, the legs may extend at generally right angles from the proximal portion 62 to establish an open rectangle profile.

Figure 13:
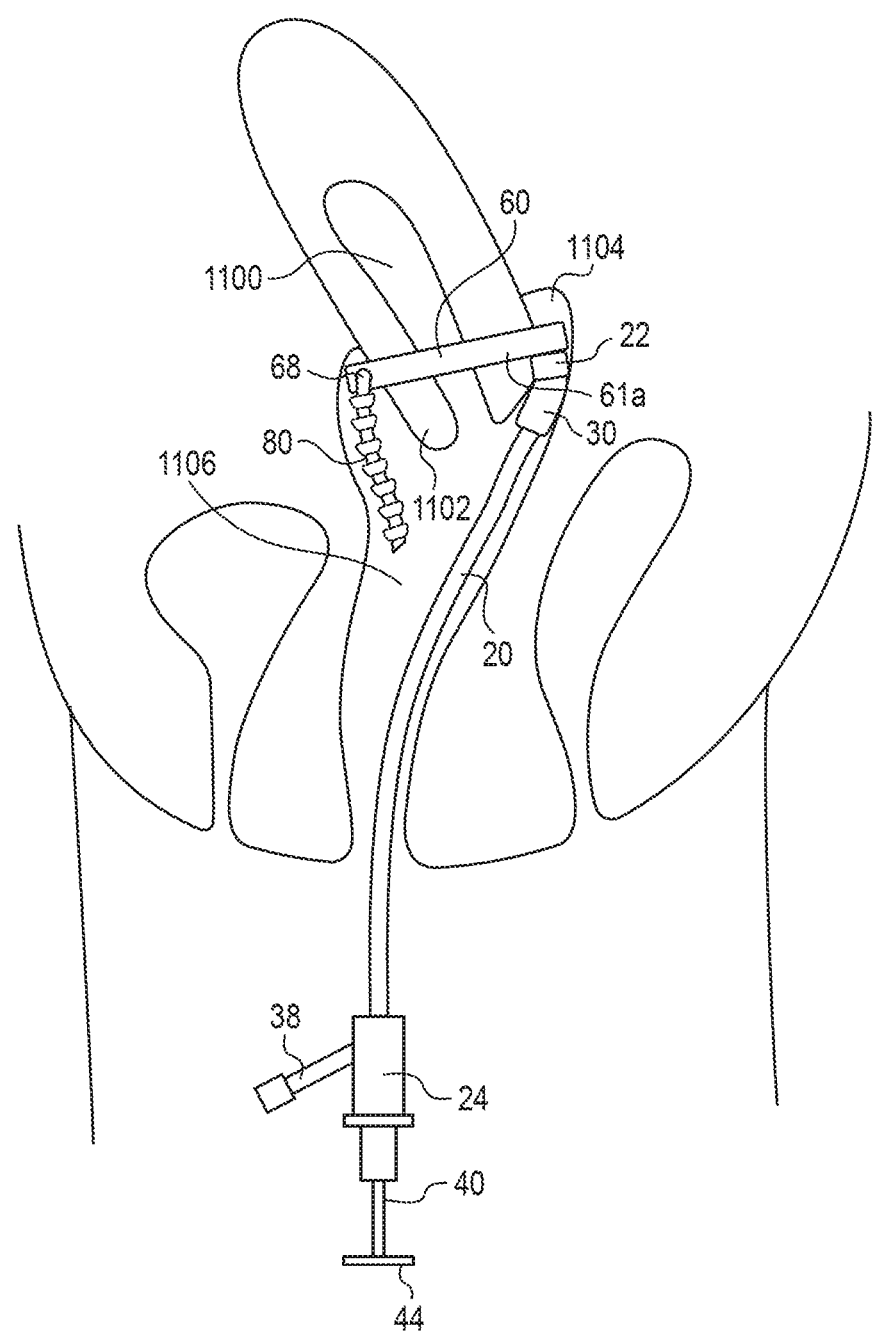
FIG. 13 is a side schematic view of a patient's vagina, cervix, and uterus, showing the device of FIG. 1 positioned therein in preparation for a cervical cerclage procedure.

Generally, the legs 61a, 61b are constructed with a shape and size such that the legs are adapted to wrap around a significant portion of a female patient's (either human or mammal) cervical tissue when the device 10 is positioned such that the grasper 60 is disposed within or abutting the posterior fornix 1104 of the patient's cervix (shown in FIG. 13). In some embodiments, the first and second legs 61a, 61b are constructed to wrap around a significant portion of a patient's cervical tissue when the balloon 30 is inflated, which compresses the cervical tissue together due to the size of the inflated balloon, within the limited space available within the patient's vagina 1106.

In some embodiments, the inner surface of the first and second legs 61a, 61b (i.e. the surface that engages the cervical tissue when positioned within the patient) include a plurality of ridges 65 that extend inwardly from the legs, which are each configured to engage the cervical tissue, and locally compress the tissue engaging the ridges 65 to assist with maintaining the position of the grasper 60 with respect to the cervical tissue before the physician has locked the grasper 60 in place, as discussed above. The plurality of ridges 65 may be disposed at consistent spaces along the length of the length of each of the first and second legs 61a, 61b (such as at every half centimeter or another clinically effective spacing). In other embodiments, the plurality of ridges 65 may only be positioned on one of the two legs 61a, 61b.

In some embodiments, an end of the arcuate member 61, and in some embodiments, an end portion of the second leg 61b may support a flexible member 80 that extends therefrom. A proximal end portion 84 of the flexible member 80 is retained by the grasper 60 (and specifically the proximal end portion of the second leg 61b) and the flexible member 80 includes an opposite distal end portion 82 that extends to a tip 83. The flexible member 80 may be an elongate string, cord, rope, tape (such as mersliene band), or thread. The flexible member 80 may be made of any flexible material that is safe for medical use for a long term engagement with cervical tissue and disposition within a patient's vagina. Some materials that may be used are silicone, urethanes, or relatively soft thermoplastics, mersilene, cotton, suture material, or various known flexible materials.

In some embodiments, the flexible member 80 may be a discrete component from the grasper 60 with a proximal end portion 84 that is fixed to the grasper 60, while in other embodiments, a portion of the flexible member 80 may extend through at least a portion of the grasper 60 (such as within a cavity formed by one or both of the first and second legs 61a, 61b) and be fixed to the grasper 60. In some embodiments, the ridges 65, upon the grasper 60 (discussed above) may be provided by the plurality of retaining elements 90 disposed along the flexible member 80 (discussed below) along the portion of the grasper 60 that engages the patient's cervical tissue.

In some embodiments, the flexible member 80 may be cylindrical, while in other embodiments, the flexible member may be a tape or a geometry with a generally oval or rectangular orientation. In embodiments where the flexible member is not cylindrical, the flexible member 80 may be configured such that the relatively wider portion contacts the cervical tissue to increase the surface area of engagement between the flexible member 80 and the cervical tissue.

The flexible member 80 may include a plurality of retention members 90 disposed along the length thereof, starting with a second end portion 84, that extends from the second leg 61b of the grasper 60, and disposed along the length of the flexible member 80 to a distal end portion 82 toward its tip 83. In some embodiments, the tip 83 may be formed as a retention member 90, while in other embodiments, the first retention member 90 may be disposed proximally of the tip 83 to allow the tip 83 to be easily threaded through the receiving aperture 68a of the receiving structure 68, discussed below.

Figure 6:
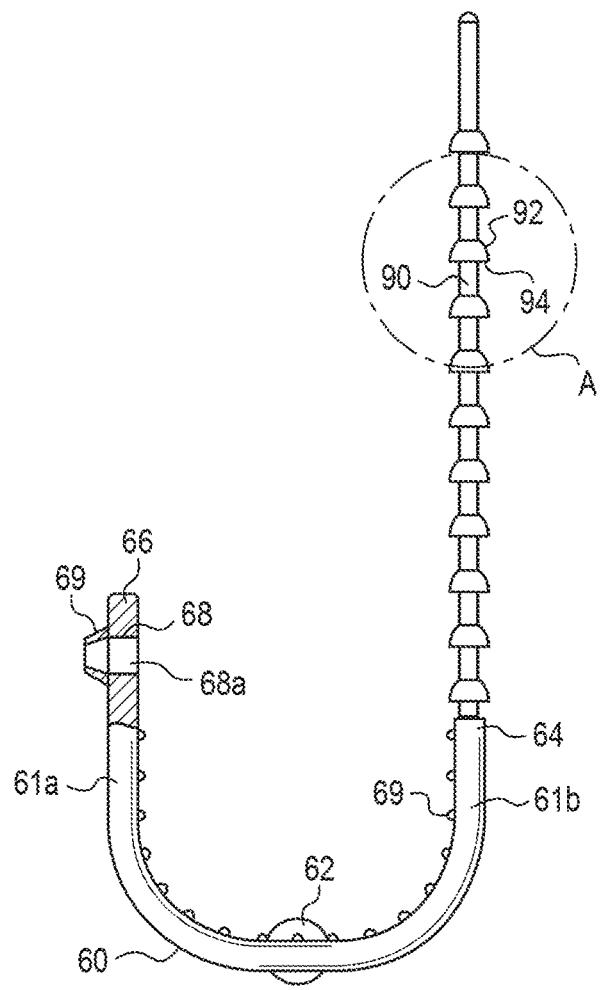
FIG. 6 is an end view of the device of FIG. 1 with a partial cross-sectional view the distal end portion of the first leg of the grasper, and showing a flexible members extending in a straight line from the second leg of the grasper.
Figure 7:
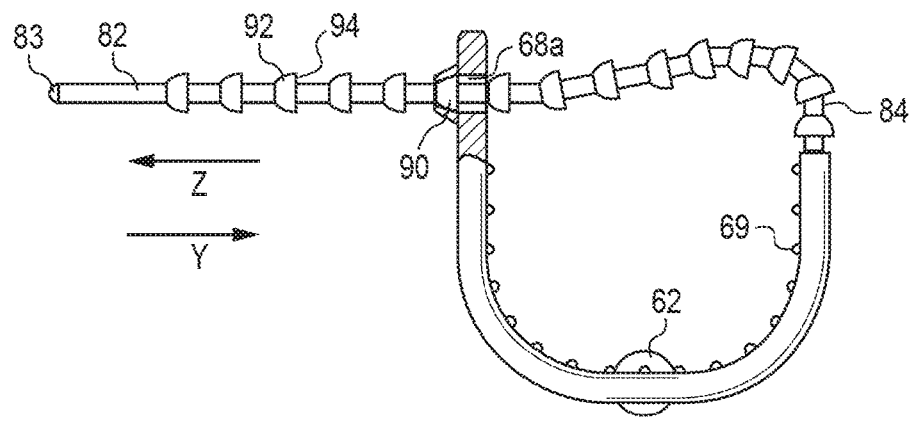
FIG. 7 is the view of FIG. 6 depicting the flexible member extending through an receiving structure in the first leg of the grasper.

The retentions members 90 are best shown in FIGS. 6 and 7. In some embodiments, each retention member 90 may be formed with the same size and geometry, and may be evenly spaced along the length of the flexible member 80. In other embodiments, the retention members 90 may be formed with different geometries along the length of the flexible member 80, such as, for example, with slightly increasing geometric profiles (such as increasing diameters) along the length of the flexible member 80 from the distal end portion 82 toward the proximal end portion 84. Increasing sized retention members 90 may be desired toward the proximal end portion 84 because the compression of the patient's cervix increases as the flexible member 80 is further pulled through the receiving structure 68 located on an end portion of the first leg 61a of the grasper should 60 be added here, and the cervical tissue when compressed places greater tension upon the flexible member 80, therefore necessitating a stronger (i.e. more surface area) connection between the locking portion 94 of the retention member 90 and the receiving structure 68 (preventing the flexible member 80 from being drawn proximally through the receiving structure 68 and therefore maintaining the cervical tissue bunched together as clinically desired).

Figure 6A:
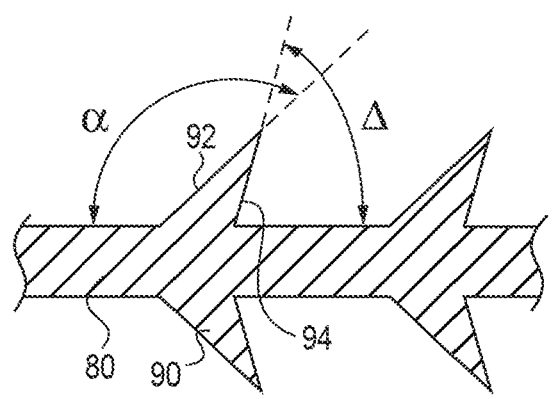
FIG. 6a is a view of detail A of FIG. 6.

As shown in FIGS. 6a and 7, each retention member 90 may include a tapered face 92 that faces toward the distal tip 83 of the flexible member 80 (when the flexible member 80 is generally straight) and an opposite locking surface 94 (that faces toward the proximal end portion 84 when the flexible member 80 is generally straight) that forms a perpendicular face, or a receding geometry (discussed below). The tapered face 92 is configured to gradually increase the diameter of the retention member 90 along its length. In some embodiments, the tapered face 92 may be geometrically conical, or in other embodiments generally conical (as shown in FIG. 6A, i.e. with an arcuate cross-sectional curve but with a radius that increases along the length of the tapered face 92). In some embodiments, the tapered face 92 may form an obtuse angle α with the longitudinal axis L of the flexible member 80 (when in a straight configuration) that forms an angle within the range of about 135 to about 160 degrees, inclusive of the angles within this range, such as e.g. 140, 145, 150, 155, 160 degrees. In embodiments where the tapered face 92 is generally conical, portions of the tapered face 92 may form different angles within this range.

The locking surface 94 may be a surface that is perpendicular to the longitudinal axis of the flexible member 80 (when in a straight configuration). In other embodiments, as shown in FIG. 6b, the locking surface 94 may form an acute angle Δ with respect to the longitudinal axis.

As mentioned above, the grasper 60 may include an arcuate member 61 that may include a first leg 61a and a corresponding second leg 61b, with the proximal end portion 62 therebetween at a connecting portion. The first leg 61a may support a receiving structure 68 at an end portion 66 thereof. The receiving structure 68 may be configured to ratchetingly receive the flexible member 80 therewith. In an exemplary embodiment, the receiving structure may initially receive the distal tip 83 of the flexible member 80 and then ratchetingly allow additional portions of the flexible member 80 to be further pulled through in a first direction Z (FIG. 7). The receiving structure 68 may be configured to resist the flexible member 80 from being pulled in the second opposite direction Y, due to engagement with the locking surface 94 of the retention member 90 engaging the receiving structure 68.

Figure 7A:
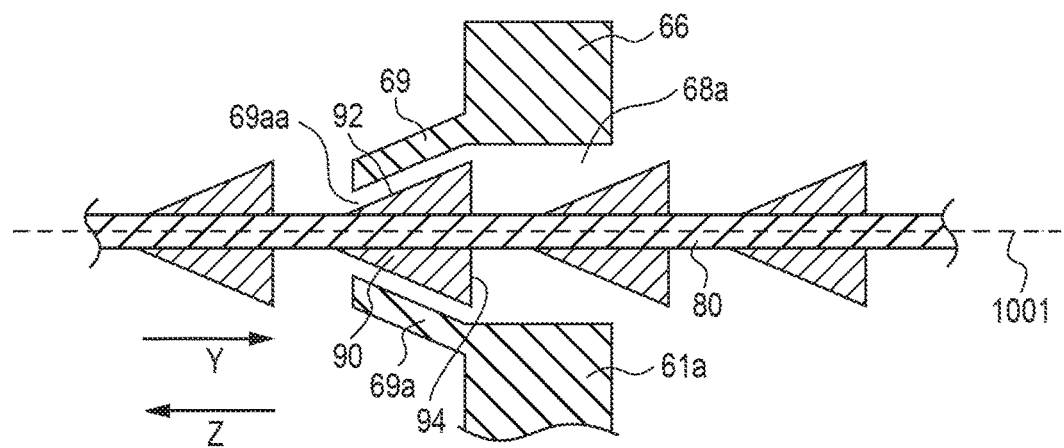
FIG. 7a is a view of detail B of FIG. 7 depicting arms of the receiving structure in their normal alignment.
Figure 7B:
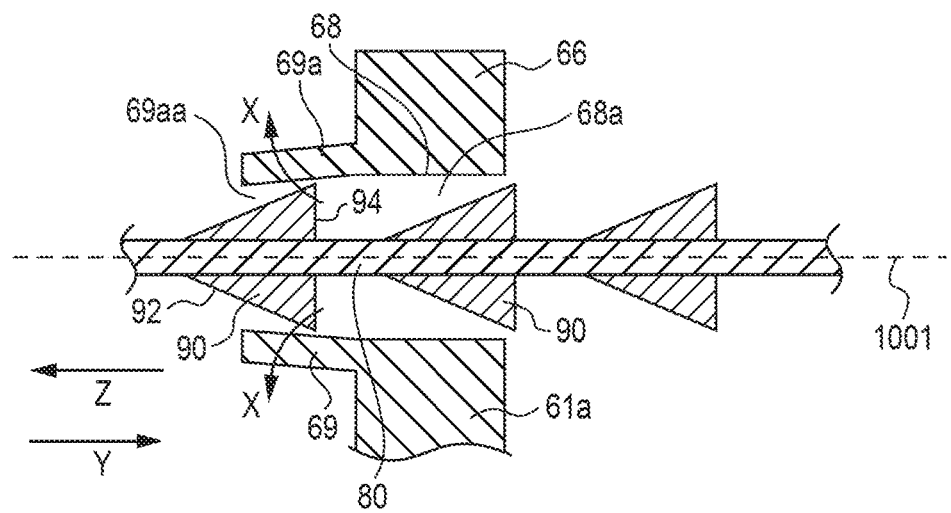
FIG. 7b is the view of FIG. 7a depicting the arms of the receiving structure being rotated outward due to engagement with a retaining portion upon the flexible member.
Figure 7C:
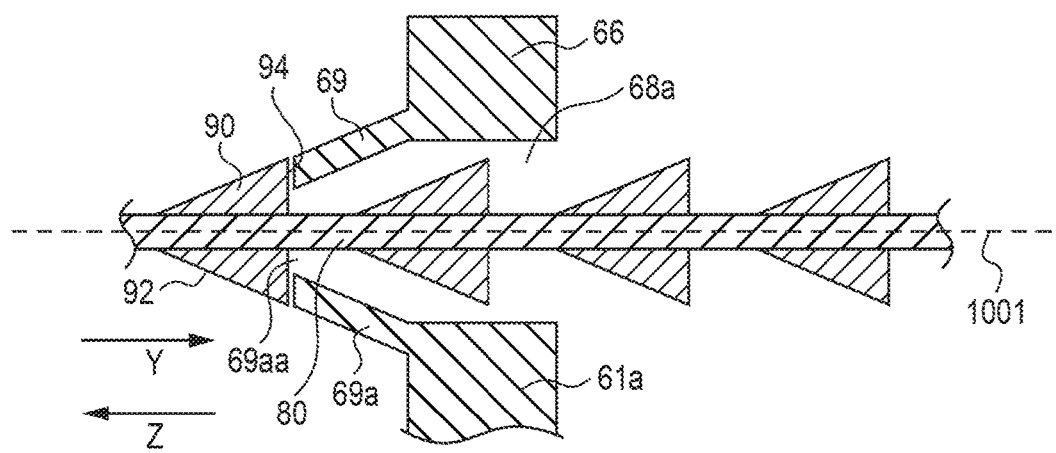
FIG. 7c is the view of FIG. 7a depicting the arms of the receiving structure blocking motion of the flexible member in the direction "Y."

As best shown in FIGS. 7a-7c, the receiving structure 68 may include an aperture 68a and a deformable portion 69, which may be disposed in registry with the aperture 68a. The deformable portion may be two or more arms 69a that are fixed to the distal end portion of the first leg 61a in a cantilevered fashion, and may be disposed at an angle with respect to the axis 1001 of the hole. As depicted in FIG. 7b, the arms 69a may be deflected or rotated radially outward in the direction X (i.e. toward a more linear orientation with respect to the outer surface of the leg 61a) to increase the size of the aperture 68a at the outer exit of the first leg 61a when the arms 69a are engaged by the tapered face 92 of a retention member 90, and with further linear movement of the flexible member and the retention member 90 in the direction Z, the arms 69 are urged further radially outward until the retention member 90 has a clear path to be pulled from the receiving structure 68.

As shown in FIG. 7c, the arms 69a may return to their normal position after the retaining portion 90 extends past the tips of the arms 69. The tips of the arms 69a may be disposed to form an aperture 69aa that is smaller than the size of the locking surface 94. The arms 69a are configured such that if the retention member 90 engages the arms 69a in the direction Y, the arms 69a do not expand to allow the retaining portion 90 to extend therethrough. The arms 69a may be either rigid in compression such that the arms generally retain their orientation pre-impact, or in embodiments, the arms 69a may flex or buckle in such a manner to reduce the size of the aperture 69aa formed therebetween, thereby preventing the retaining portion 90 from extending therepast in the direction Y.

Figure 3:
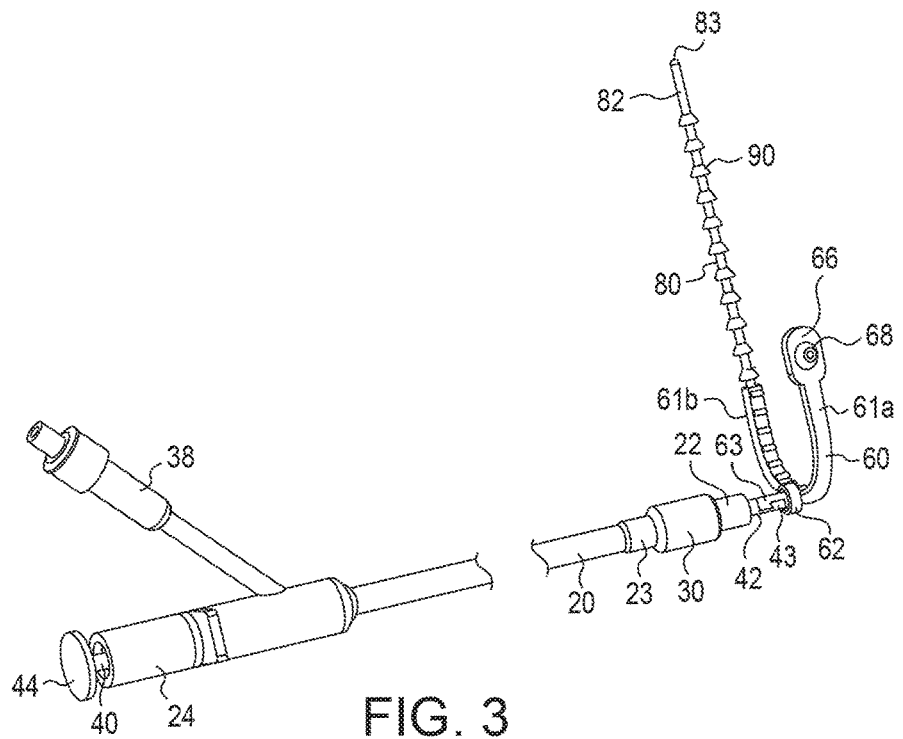
FIG. 3 is the view of FIG. 2 depicting the fingers of the stylet and the grasper slid distally outside of the catheter.
Figure 3A:
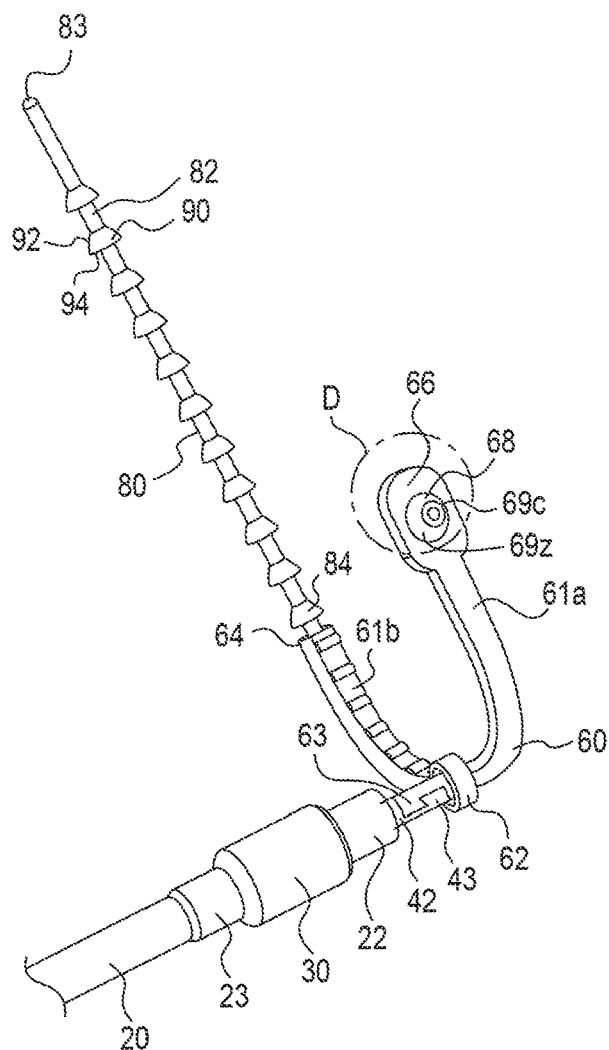
FIG. 3a is a detail view of the distal end portion of the catheter and the grasper, showing the fingers of the stylet and the grasper slid distally and outside of the hollow portion of the catheter.
Figure 3B:
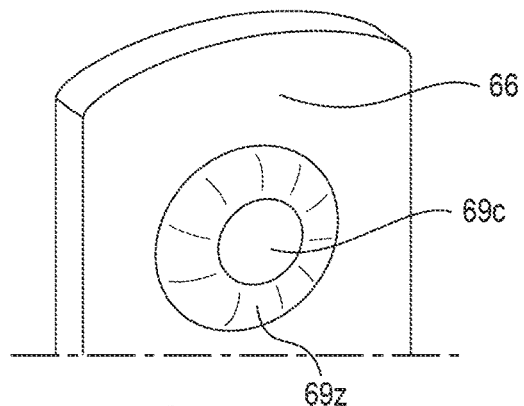
Figure 4:
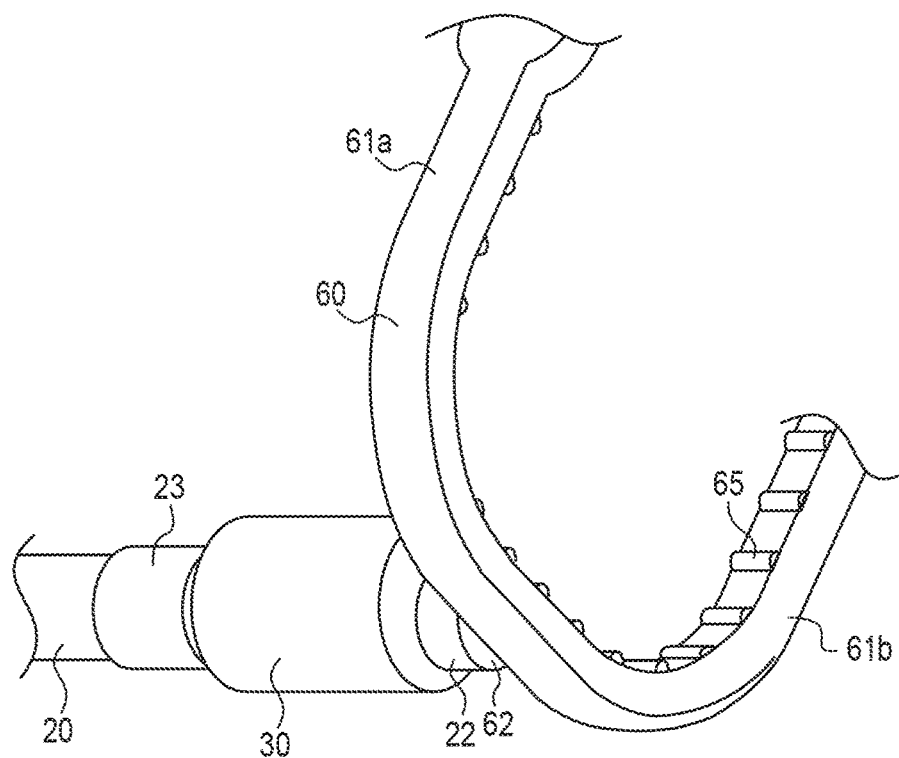
FIG. 4 is a view of detail C of FIG. 1, showing the fingers of the stylet and the grasper disposed within the hollow portion of the catheter.
Figure 5:
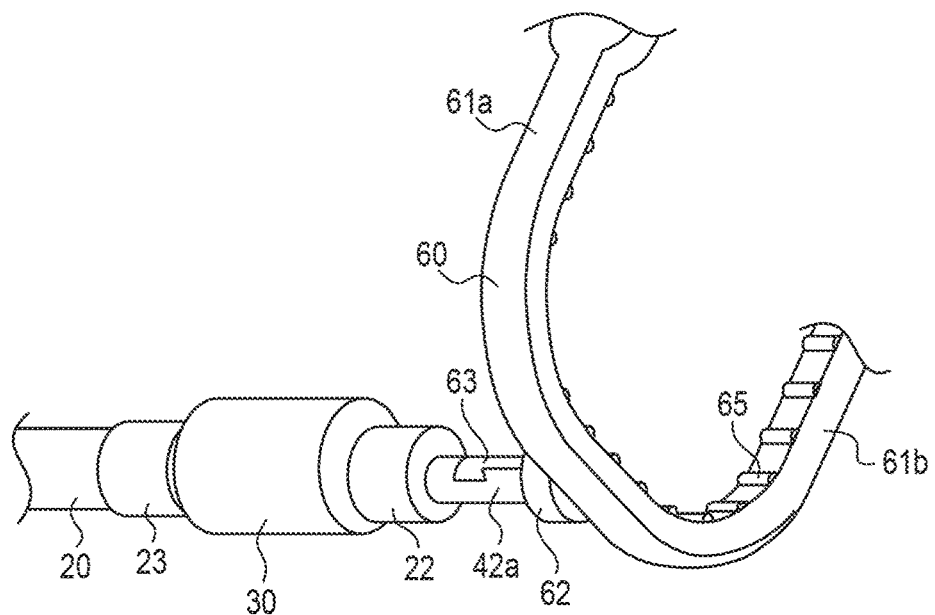
FIG. 5 is the view of FIG. 4 showing the fingers of the stylet and the grasper slid distally outside of the catheter.

In other embodiments, the deformable portion 69 may be a flexible hollow conical member 69z (FIGS. 3a, 3b, 9), which extends outward from the first leg 61a in registry with the aperture 68a, and includes an outer aperture 69c that is smaller than the diameter of the aperture 68a. In some embodiments the outer aperture 69c may be just larger than the size of the flexible member 80 and formed with a similar shape as the flexible member 80, but with a diameter/size that is smaller than the diameter/size of the locking surface 94 of the retention member 90. This type of deformable portion 69 may be formed from a stretchable yet resilient material that may expand outwardly to allow the retention member 90 to extend therethrough in direction Z (and specifically as stretched by the gradually increasing size of the tapered face 92), but not be urged to expand when the locking surface 94 approaches the deformable portion 69 in the direction Y.

Figure 17:
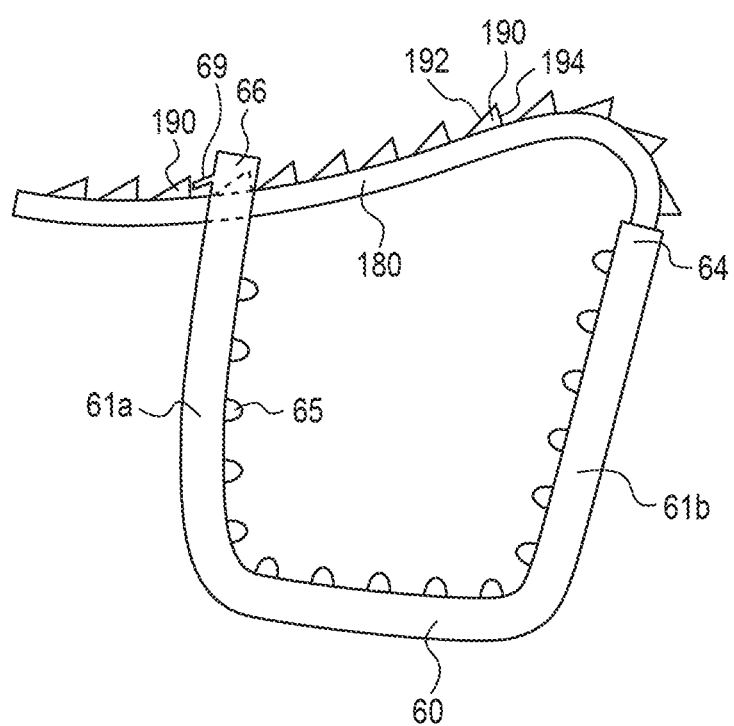
FIG. 17 is a perspective view of a grasper for use with the device of FIG. 1 with an alternate flexible member.

As depicted in FIG. 17, an alternate flexible member 180 may extend from the grasper 60, and specifically from the second leg 61b of the grasper. The flexible member 180 may include a plurality of retention members 190 disposed therealong, such as at equal spacing along the length of the flexible member 180 or at varied spacing along the length of the flexible member 180. The flexible member 180 may include a rectangular or oval cross-section with the larger dimensioned side normally forming an engaging surface that is configured to contact and close the cervical tissue disposed in conjunction with the grasper 60. The opposite side of the flexible member 180 (i.e. the other side with the larger dimension) supports the plurality of retention members 190. Similar to the retention members 90 discussed above, each of the retention members 190 may extend outward from the flexible member 180 and may include a tapered face 192 that faces toward the distal tip 183 of the flexible member 180 (when the flexible member 180 is generally straight) and an opposite locking surface 194 (that faces toward the proximal end portion 184 when the flexible member 180 is generally straight) that forms a perpendicular face, or a receding geometry (discussed below).

As shown in FIG. 17, the retention members 190 may have a general triangular cross-section, or may be modified from a geometric triangular cross-section in embodiments where the tapered face 192 is arcuate (but with a generally increasing height along its length) and be formed with a profile that includes surfaces at the angle α (as depicted in FIG. 6a with respect to the retention member 90) and/or where the locking surface 194 is formed with an orientation with an acute angle similar to the acute angle Δ shown in FIG. 6A with respect to the retention member 90. The tapered face 192 is configured to gradually increase the height of the retention member 90 along its length.

The locking surface 194 may be a surface that is perpendicular to the longitudinal axis of the flexible member 180 (when in a straight configuration). In other embodiments, the locking surface 194 may form an acute angle Δ with respect to the longitudinal axis (similar to the angle formed by the locking surface 94 depicted in FIG. 6A).

In embodiments where the retention member 190 and flexible member 180 are provided, the grasper 60 may have a receiving portion 68 that corresponds to slidingly and ratchetingly receive the distal tip 183 and then with further sliding of the flexible member 180 in the direction Z, the one and more of the plurality of retention members 190 are slidingly and ratchetingly received through the receiving portion 68 in the direction Z, but prevents motion of the flexible member 180 in the direction Y. The receiving portion 68 may be constructed with arms (similar to the arms 69), a cone, similar to cone 68z, or other structures to slidingly and ratchetingly receive the retention members 190, and one of ordinary skill in the art will comprehend suitable designs for the receiving portion 68 to work with the retention members 190 with a thorough review of this specification.

As discussed above, the catheter 20 may include a stylet 40 slidably disposed within a lumen 21. The stylet 40 extends to a distal end portion 42 that includes a finger 43 to a proximal end portion that includes an operator 44, which extends outside of the proximal end portion 24 of the catheter 20. The stylet 40 is slidable within the catheter 20 between a retracted position (FIG. 2) where the finger 43 is disposed within the lumen 21 and does not extend distally out of the catheter 20, and an extended position (FIG. 3) where the finger 43 extends distally out of the lumen 21. The operator 44 may be directly mounted to the stylet 40 such that movement of the operator 44 causes sliding motion of the stylet 40 (and therefore the finger 43) in the same direction.

Figure 8:
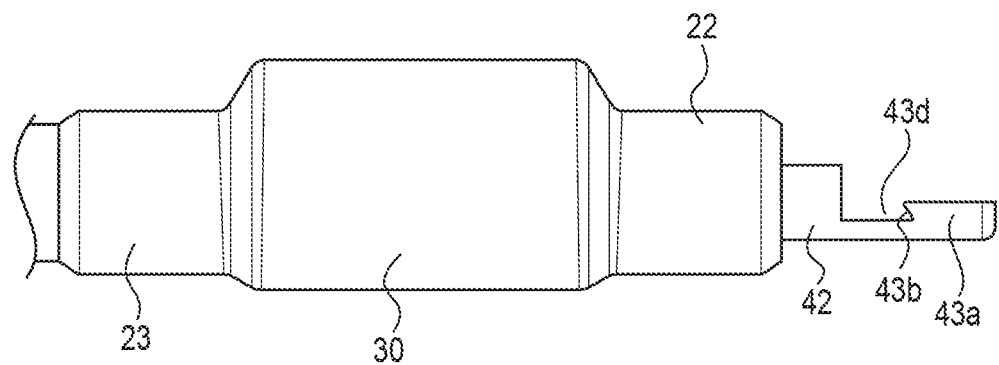
FIG. 8 is a side view of the distal end portion of the device of FIG. 1 with the finger slid distally outside of the hollow portion 21 of the catheter.
Figure 9:
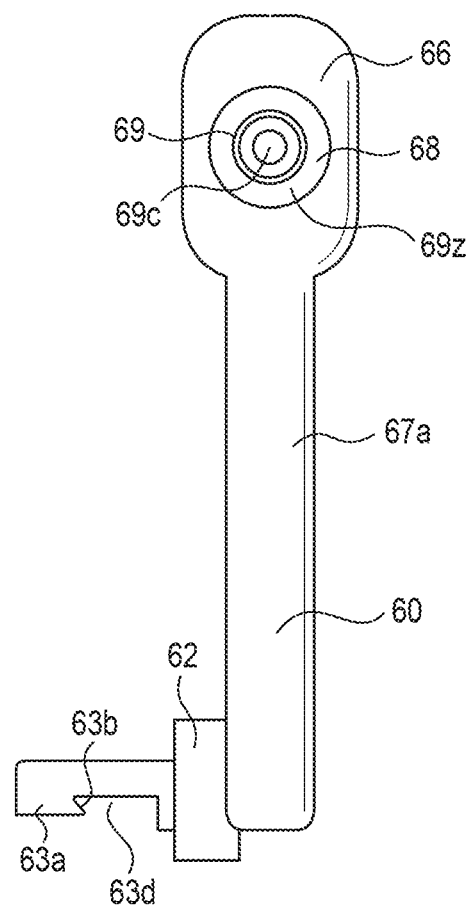
FIG. 9 is a side view of the grasper of the device of FIG. 1.
Figure 10:
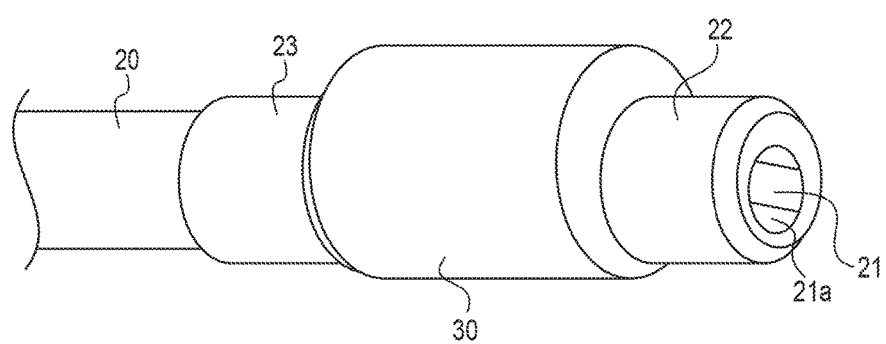
FIG. 10 is a perspective portion of the distal end portion of the catheter of FIG. 1.
Figure 11:
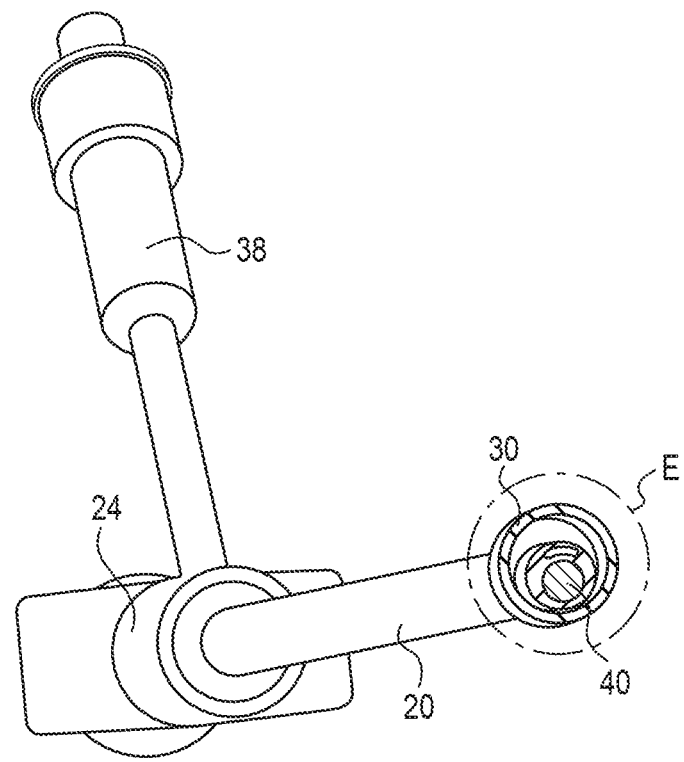
FIG. 11 is a sectional view of the catheter and balloon of the device of FIG. 1 depicting the stylet extending through the lumen.
Figure 11A:
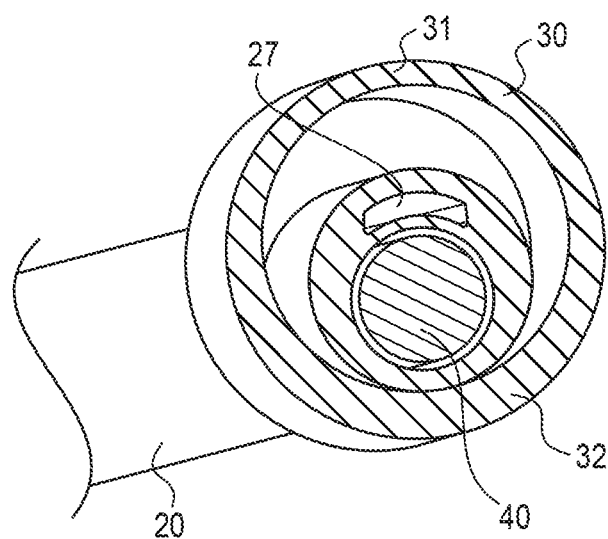
FIG. 11a is a view of detail E of FIG. 11.
Figure 12:
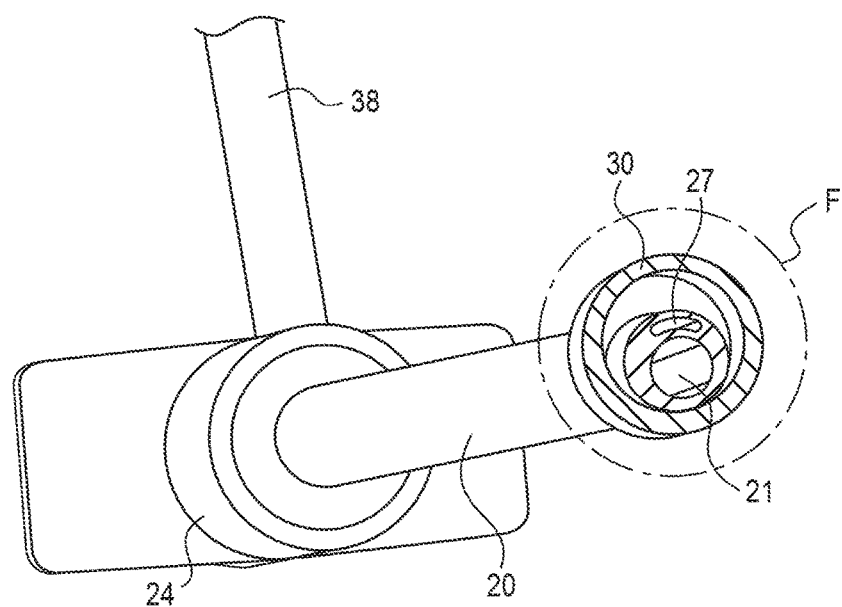
FIG. 12 is the view of FIG. 11 with the stylet removed.
Figure 12A:
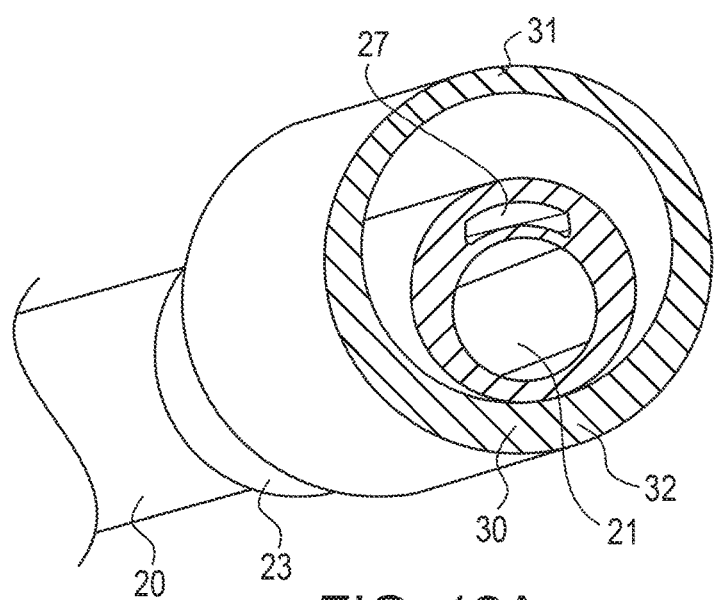
FIG. 12a is a view of detail F of FIG. 12.

As best shown in FIGS. 8 and 9, the finger 43 of the stylet 40 is configured to matingly receive a corresponding finger 63 that extends from a proximal portion 62 of the grasper 60. The fingers 43 and 63 may be sized and shaped to engage each other and to prevent linear motion of the grasper linearly away from the stylet 40. In some embodiments, each finger 43, 63 includes a ledge 43a, 63a, respectively, and an inclined portion 43b, 63b, respectively, that extends from the ledge. The inclined portions of each finger 43, 63 may be formed from the same (or very similar) angle such that the two inclined portions mate together. In some embodiments, the inclined portions 43, 63 may each form an acute angle with respect to the length of the respective finger, while in other embodiments, the inclined portions 43, 63 may each be formed with a substantially perpendicular surface to the length of the finger. Each finger also may include a void 43d, 63d that is the size and shape of the ledge of the opposite finger such that the combined fingers form a compact configuration, which in some embodiments may be a cylindrical configuration with a diameter just smaller than the hollow portion 21a of the lumen 21 at the distal end portion 22 of the catheter 20, which provides space for the mated fingers 43, 63 to be slid into the hollow portion 21a, such as by withdrawing the operator 44 of the stylet 40 proximally from the proximal end portion 24 of the catheter 20. As can be understood, when the engaged fingers 43, 63 are disposed within the hollow portion 21a, the grasper 60 is fixed to the catheter 20. When the engaged fingers 43, 63 are slid distally out of the hollow portion 21a, the engaged fingers 43, 63 can be disengaged by relative lateral motion of one finger with respect to the other finger.

A balloon 30 may be disposed upon the distal end portion 22 of the catheter 20 and may be selectively inflated and deflated by the operator, such as a through a luer lock or similar fitting 38, which is fluidly connected with the balloon through a lumen 27. The balloon 30 may be a conforming or non-confirming balloon.

Figure 16A:
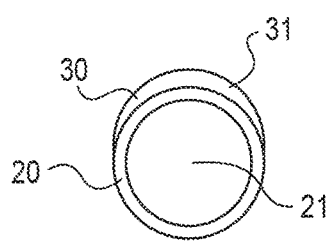
FIG. 16a is a schematic view of a balloon suitable for the catheter of FIG. 1 with the balloon deflated.
Figure 16B:
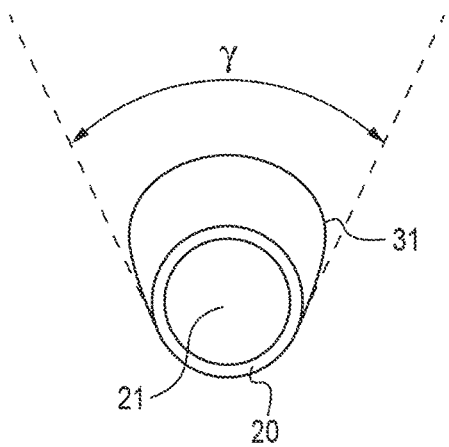
FIG. 16b is the view of FIG. 16a with the balloon inflated.
Figure 16C:
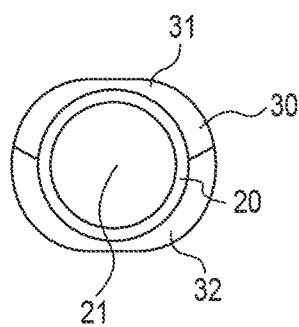
FIG. 16c is a schematic view of another balloon suitable for the catheter of FIG. 1 with the balloon deflated.
Figure 16D:
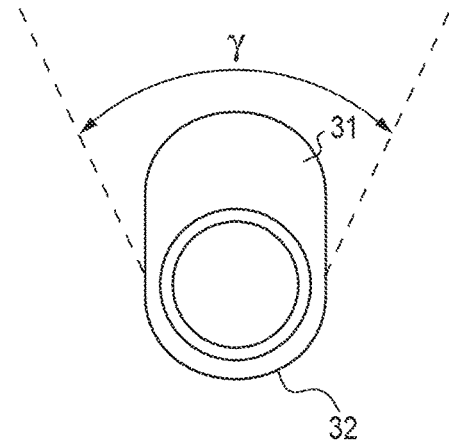
FIG. 16d is the view of FIG. 16c with the balloon inflated.

In some embodiments shown schematically in FIGS. 16a-16d, a first portion 31 of the balloon 30 may extend for a first portion of the circumference of the catheter, such as an arc length γ, and is configured to inflate away from the nominal diameter of the catheter 20 at a distance greater than the a second portion 32 of the balloon 30 is configured to inflate (FIGS. 16c, 16d), or in other embodiments, the balloon 30 may only extend along the arc length γ of the circumference of the catheter 20 (FIGS. 16a, 16b). The balloon 30 may be provided with a more stretchable or resilient material around the first portion 31, than the stretchability or resilience of the material in the opposite second portion 32 (when provided). This difference in stretchability or resilience may be due to a thicker material forming the second portion of the balloon 32 than the first portion 31, or differing materials, with different stretchabilities or resilience characteristics forming the different portions of the balloon 30, or with other structures. In other embodiments, the first and second portions 31, 32 may be different balloons and may be inflated separately (which may be through different lumens).

In some embodiments the first portion 31 of the balloon 30 (or the entire balloon 30 when defined around less than the entire circumference of the catheter 30) may extend for a range of about 90 degrees (or ¼) of the total circumference of the catheter 20. Alternatively other ranges may be appropriate, such as 45 degrees of circumference, 135 degrees, 180 degrees, or any clinically suitable range (such a range to allow the balloon 30 to compress the cervical tissue prior to compressing with the flexible member 80, and to minimize the movement of the catheter within the vagina that might occur if the balloon also inflates to the same extent (or at all) in directions away from the cervical tissue), such as e.g. 45 degrees, 60 degrees, 150 degrees, 160 degrees, and 180 degrees, including all specific circumferences within this range. In other embodiments, a balloon 30 that is inflatable to generally the same radial distance around the entire circumference of the balloon may be provided.

Figure 14:
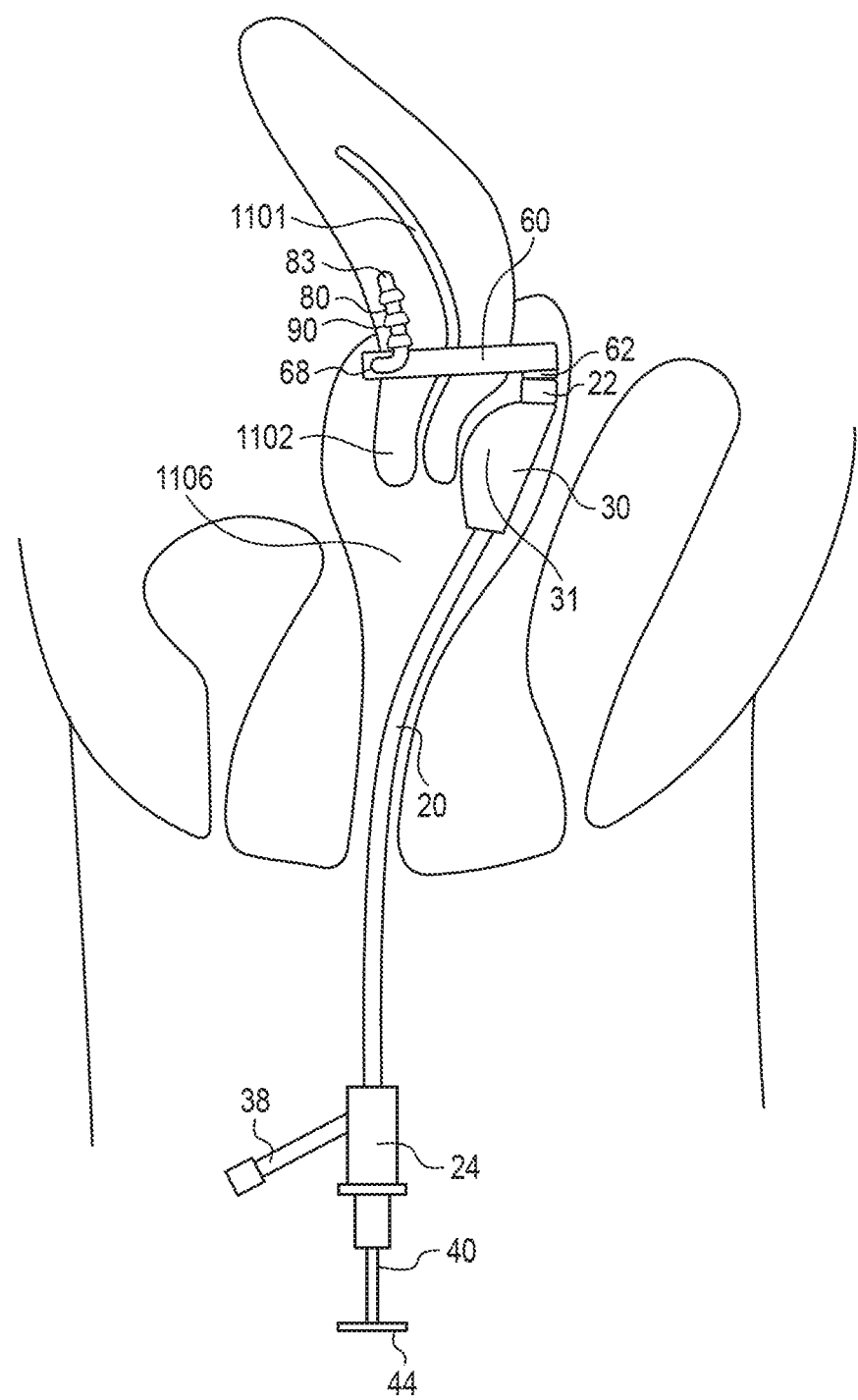
FIG. 14 is the view of FIG. 13 with the balloon expanded and the flexible member threaded through the receiving structure.
Figure 15:
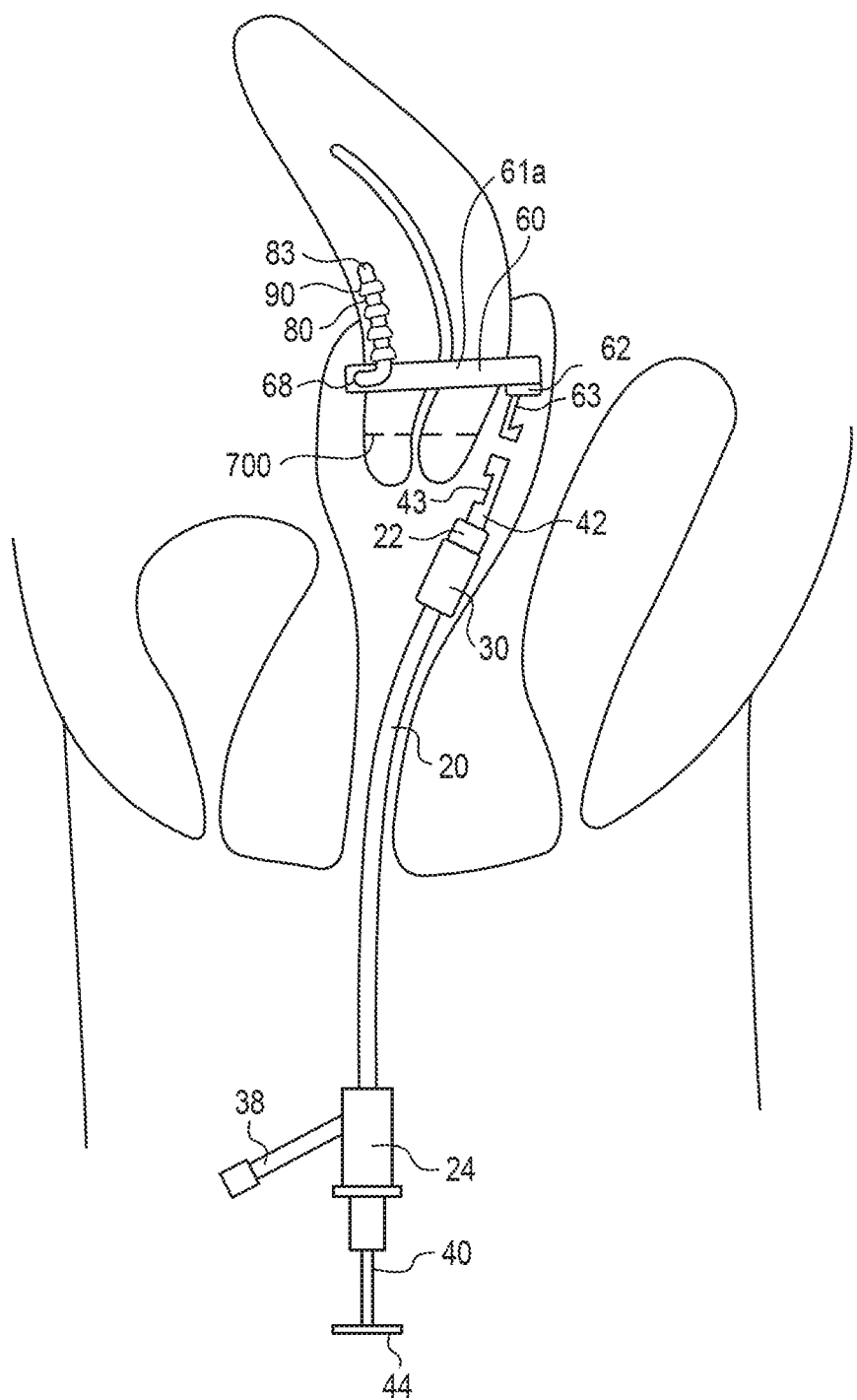
FIG. 15 is the view of FIG. 13 with the cervical cerclage stitching completed and the catheter released from the grasper.

Turning now to FIGS. 13-15, the device 10 is depicted within a patient's vagina 1106 with the proximal end 62 of the grasper 60 proximate to or within the posterior fornix 1104 of a patient's cervix 1102. In FIG. 13, the grasper 60 is properly positioned, and the first leg 61a is around the patient's cervix 1102, and the second leg 61b (not visible with the view of FIG. 13) is wrapped around the opposite side of the patient's cervix 1102. As shown in FIG. 14, the balloon 30 may be inflated which compresses the cervical tissue 1102 together to prevent any communication from the vagina 1106 to the uterus 1100.

With the balloon 30 (as discussed above) inflated, the distal tip 83 of the flexible member 80 is threaded through the aperture 69 upon the receiving structure 68 in the distal end portion of the first leg 61b and the flexible member 80 is pulled through the aperture 69 until the cervical tissue therebetween is suitable compressed. When the flexible member 80 is sufficiently pulled through the aperture 69 to establish the correct compression of the cervical tissue, the flexible member 80 may be released, and the position of the flexible member 80 is maintained due to the interaction between the receiving structure, and specifically the arms 69a, or similar structure, and the locking portion 94, which prevents the retaining portion 90 next to the receiving structure 68 from extending through the arms 69a and into the aperture 68a in the direction Y.

Upon properly tightening the flexible member 80, the balloon 30 may be deflated. Next, the grasper 60 may be released from the catheter 20. While holding the catheter 20 still, the operator 44 of the stylet 40 may be urged distally, which pushes both the finger 43 upon the distal end portion 42 of the stylet 40, as well as the grasper 60 (based upon the engagement of the finger 63 extending from the proximal end portion 62 of the grasper 60) distally out of the hollow portion 21a of the catheter 20 and distally away from the catheter 20. Upon sliding motion out of the hollow portion 21a, the engaged fingers 43, 63 may be disengaged by laterally sliding one of the finger away from the other finger. Once the fingers are laterally slid apart, the stylet 40 is released from the grasper 60, and the catheter 20 (including the stylet 40) may be removed from the patient, with the grasper 60 remaining within the patient, as shown in FIG. 15.

With the catheter 20 removed from the patient, the physician may complete the cervical stitch procedure as clinically indicated, and as schematically depicted in FIG. 15 as element 700. After the cervical stitch procedure, or at another clinically appropriate time under the determination of the physician, the grasper 60 may be removed from the patient after the flexible member 80 is cut, thereby releasing the compression within the cervical tissue.

While the preferred embodiments of the disclosure have been described, it should be understood that the disclosure is not so limited and modifications may be made without departing from the disclosure. The scope of the invention is defined by the appended claims, and all devices that come within the meaning of the claims, either literally or by equivalence, are intended to be embraced therein.

The invention claimed is:

1. A medical device, comprising:
   a grasper configured to allow gripping and compression of a patient's cervix when disposed proximate a patient's cervix;
   an elongate catheter comprising a distal portion that is selectively releaseably connectable to the grasper, the grasper comprises at least one leg and is adapted to interact with at least a portion of a patient's cervix when deployed, and a flexible member that extends from a first end portion of the grasper, with a proximal end portion retained by the grasper and an opposite distal end portion extending away from the grasper to a distal tip,
   wherein the distal portion of the catheter further comprises an inflatable balloon, and a proximal portion opposite from the distal portion, the proximal portion being configured to allow selective inflation and deflation of the balloon.

2. The medical device of claim 1, wherein the flexible member comprises a plurality of retention features that are spacingly disposed along a length of the flexible member between the distal tip and the proximal end portion.

3. The medical device of claim 2, wherein the grasper further comprises a second end portion, the second end portion includes a receiving structure that is arranged to interact and retain a portion of the flexible member.

4. The medical device of claim 3, wherein the receiving structure is an aperture that is configured to threadably receive a portion of the flexible member therethrough.

5. The medical device of claim 4, wherein the receiving structure is configured to ratchetingly receive the flexible member, wherein the receiving structure engages one of the plurality of retention features and allows the flexible member to continue to extend through the aperture in a first direction such that a location of engagement between the receiving structure and the flexible member becomes closer to the proximal end portion of the flexible member.

6. The medical device of claim 5, wherein each of the plurality of retention features are circular, with a tapered portion facing toward the distal tip and a generally perpendicular portion facing toward the proximal end portion.

7. The medical device of claim 2, wherein each of the plurality of retention features are circular, with a tapered portion facing toward the distal tip and a generally perpendicular portion facing the proximal end portion.

8. The medical device of claim 2, wherein each of the plurality of retention features include a tapered portion facing toward the distal tip and a generally perpendicular portion facing the proximal end portion.

9. The medical device of claim 2, wherein each of the plurality of retention features include a tapered portion that faces the distal tip with a face that forms an obtuse angle with respect to a surface of the retention feature just distal of the retention feature, and an angled portion that faces the proximal end portion and forms an acute angle with respect to a surface of the retention feature just proximal of the retention feature.

10. The medical device of claim 1, wherein a distal tip of the catheter includes a hollow portion, and wherein when the catheter is connected to the grasper, a proximal portion of the grasper is disposed within the hollow portion.

11. The medical device of claim 10, wherein the catheter further comprises a stylet slidably disposed within a lumen of the catheter, a distal end portion of the stylet includes a finger that is configured to matingly engage the proximal portion of the grasper, and wherein the finger and the proximal portion are fixed together when the mating engagement is disposed within the hollow portion.

12. The medical device of claim 11, wherein the stylet comprises an operator that is disposed to control linear sliding movement of the stylet with respect to the catheter, wherein linear sliding movement of the stylet urges corresponding linear sliding movement of the grasper when the finger is matingly engaged with the proximal portion of the grasper.

13. The medical device of claim 11, wherein the finger and the proximal portion of the grasper are capable of disengaging when the stylet is slid such that the engaging finger and proximal portion of the grasper are outside of the hollow portion.

14. The medical device of claim 1, wherein the inflatable balloon is configured to inflate radially outward along an arc length of the circumference of the catheter that is less than an entire circumference of the catheter.

15. The medical device of claim 14, wherein the inflatable balloon in configured to extend radially outward about an arc length of about 135 degrees.

16. A medical device, comprising:
   a grasper configured to allow gripping and compression of a patient's cervix when disposed proximate a patient's cervix;
   an elongate catheter comprising a distal portion that is selectively releaseably connectable to the grasper, the grasper is adapted to interact with at least a portion of a patient's cervix when deployed, and a flexible member that extends from a first end portion of the grasper, with a proximal end portion retained by the grasper and an opposite distal end portion extending away from the grasper to a distal tip, wherein the flexible member comprises a plurality of retention features that are spacingly disposed along a length of the flexible member between the distal tip and the proximal end portion and the grasper further comprises a second end portion, the second end portion includes a receiving structure that is arranged to interact with and retain a portion of the flexible member, wherein a distal tip of the catheter includes a hollow portion, and wherein when the catheter is connected to the grasper, a proximal portion of the grasper is disposed within the hollow portion, wherein the distal portion of the catheter further comprises an inflatable balloon, and a proximal portion opposite from the distal portion, the proximal portion being configured to allow selective inflation and deflation of the balloon.

17. The medical device of claim 16, wherein the catheter further comprises a stylet slidably disposed within a lumen of the catheter, a distal end portion of the stylet includes a finger that is configured to matingly engage the proximal portion of the grasper, and wherein the finger and the proximal portion are fixed together when the mating engagement is disposed within the hollow portion.

18. The medical device of claim 17, wherein the finger and the proximal portion of the grasper are capable of disengaging when the stylet is slid such that the engaging finger and proximal portion of the grasper are outside of the hollow portion.

19. The medical device of claim 17, wherein the stylet comprises an operator that is disposed to control linear sliding movement of the stylet with respect to the catheter, wherein linear sliding movement of the stylet urges corresponding linear sliding movement of the grasper when the finger is matingly engaged with the proximal portion of the grasper.

20. The medical device of claim 16, wherein the inflatable balloon is configured to inflate radially outward along an arc length of the circumference of the catheter that is less than an entire circumference of the catheter.

* * * * *